US010857015B2

(12) United States Patent
Argentine

(10) Patent No.: US 10,857,015 B2
(45) Date of Patent: Dec. 8, 2020

(54) VARIABLE SPEED RETRACTION MECHANISM DELIVERY SYSTEM AND METHOD

(71) Applicant: Medtronic Vascular, Inc., Santa Rosa, CA (US)

(72) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 216 days.

(21) Appl. No.: 15/927,120

(22) Filed: Mar. 21, 2018

(65) Prior Publication Data
US 2019/0290462 A1 Sep. 26, 2019

(51) Int. Cl.
*A61F 2/966* (2013.01)
*A61F 2/95* (2013.01)

(52) U.S. Cl.
CPC ............ *A61F 2/966* (2013.01); *A61F 2/9517* (2020.05); *A61F 2/9522* (2020.05); *A61F 2002/9511* (2013.01)

(58) Field of Classification Search
CPC .............. A61F 2/966; A61F 2002/9511; A61F 2002/9517; A61F 2002/9522; A61F 2002/9665
USPC ........................................................ 623/1.11
See application file for complete search history.

(56) References Cited

U.S. PATENT DOCUMENTS

| 5,829,737 | A | 11/1998 | Gersemsky |
|---|---|---|---|
| 7,105,016 | B2* | 9/2006 | Shiu .......................... A61F 2/95 623/1.12 |
| 7,935,141 | B2 | 5/2011 | Randall et al. |
| 7,976,574 | B2 | 7/2011 | Papp |
| 2006/0058866 | A1* | 3/2006 | Cully ......................... A61F 2/95 623/1.11 |
| 2011/0288558 | A1* | 11/2011 | Nimgaard ................. A61F 2/95 606/108 |
| 2011/0313506 | A1* | 12/2011 | Ray ................... A61B 17/12022 623/1.12 |
| 2015/0250631 | A1* | 9/2015 | Cummins ............... A61F 2/966 606/108 |
| 2017/0196352 | A1* | 7/2017 | King .................. A47B 21/0314 |

OTHER PUBLICATIONS

EP Application No. 19163446.8, Extended European Search Report, dated Oct. 22, 2019, 9pages.

* cited by examiner

Primary Examiner — Martin T Ton

(57) ABSTRACT

A sheath of a delivery system is retracted by winding in cords coupled to the sheath. More particularly, a helical reel is rotated to wind the cords into a helical cord groove and retract the sheath. Rotation of the helical reel simultaneously causes a cord feed ring to slide ensuring that that the cords are correctly fed into the helical cord groove through cord feedthrough apertures of the cord feed ring. Initially, due to a minimal diameter of the helical cord groove, the cords are retracted slowly and with a high amount of torque, e.g., a high mechanical advantage. After retraction of the sheath has begun, the speed of retraction of the sheath is increased with reduced torque as the cords are wound around the increasing diameter of the helical cord groove.

11 Claims, 5 Drawing Sheets

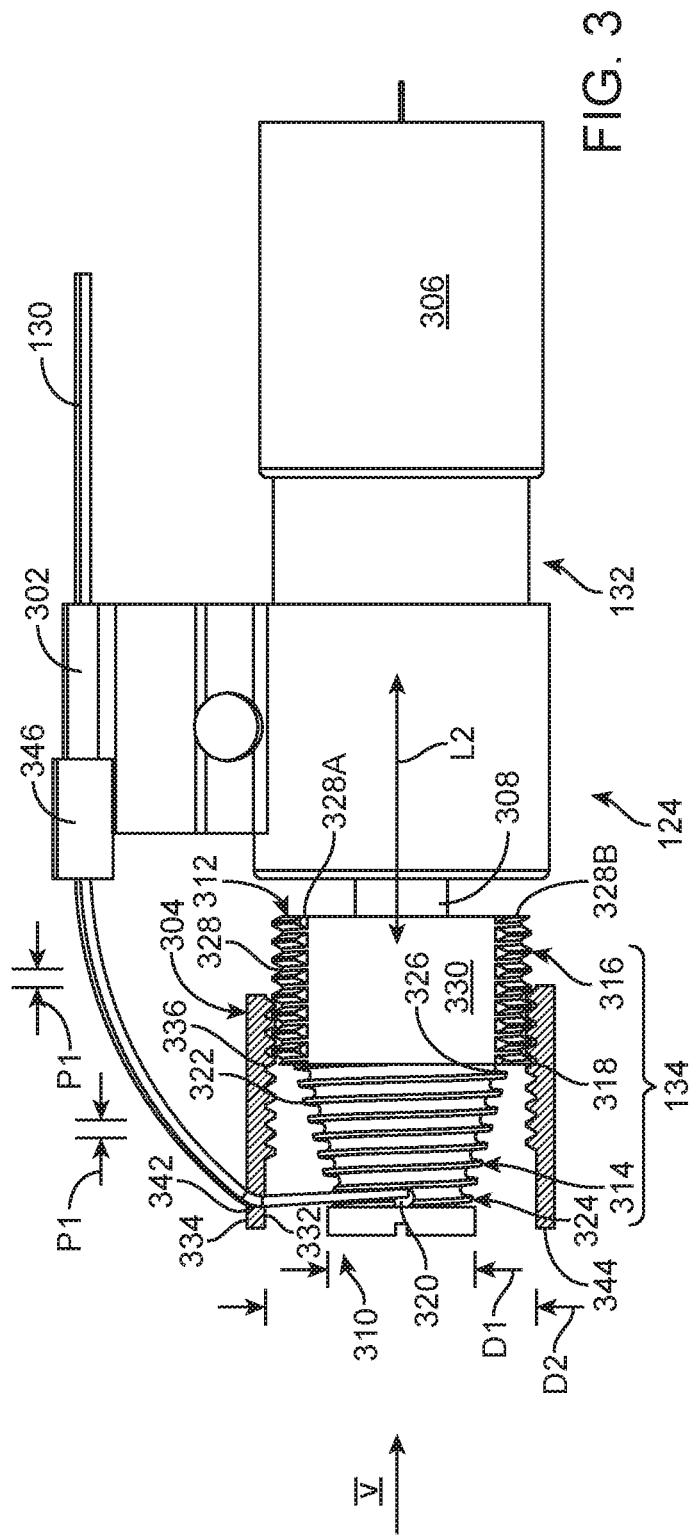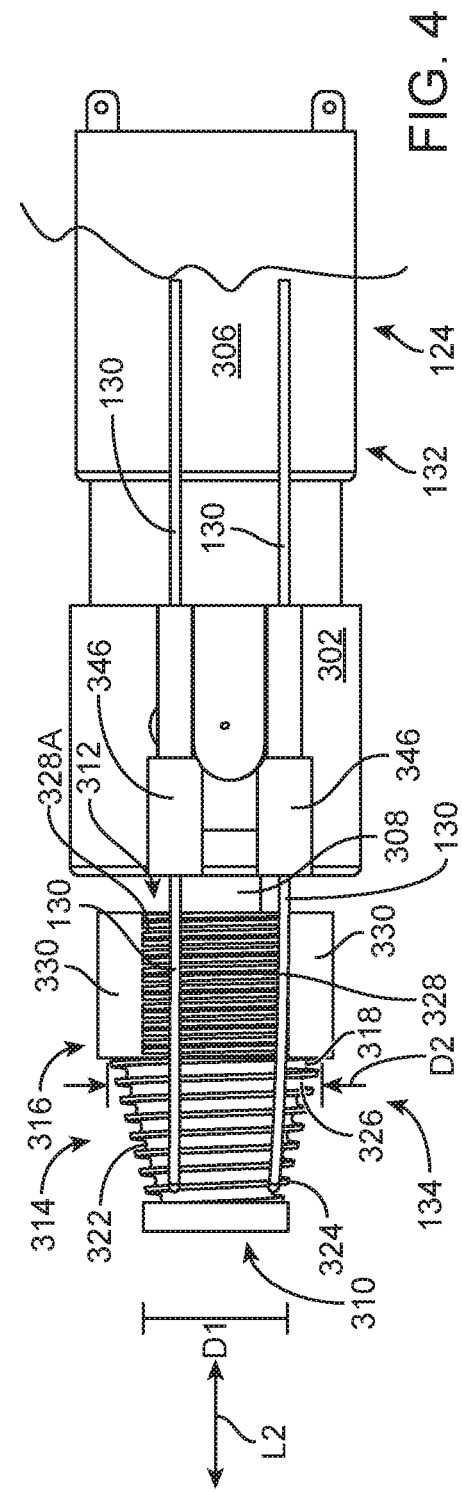

VARIABLE SPEED RETRACTION MECHANISM DELIVERY SYSTEM AND METHOD

BACKGROUND

Field

The present application relates to an intra-vascular device and method. More particularly, the present application relates to a device for treatment of intra-vascular diseases.

Description of the Related Art

A conventional stent-graft (endovascular prosthesis) typically includes a radially expandable reinforcement structure, formed from a plurality of annular stent rings, and a cylindrically shaped layer of graft material defining a lumen to which the stent rings are coupled. Stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

The stent-graft is typically delivered within a sheath to the deployment location. The sheath is then retracted to expose the stent-graft. To allow accurate positioning and rapid deployment of the stent-graft, the delivery system should impart a significant, yet controlled, force to retract the sheath.

SUMMARY

A sheath of a delivery system is retracted by winding in cords coupled to the sheath. More particularly, a helical reel is rotated to wind the cords into a helical cord groove and retract the sheath. Rotation of the helical reel simultaneously causes a cord feed ring to slide ensuring that the cords are correctly fed into the helical cord groove through cord feedthrough apertures of the cord feed ring.

Initially, due to a small diameter of the helical cord groove, the cords are retracted slowly and with a high amount of torque, e.g., a high mechanical advantage. This allow the physician to verify the accuracy of the deployment position as the prosthesis engages the surrounding body lumen. Further, the initial high torque overcomes the initial high static frictional forces associated with retracting the sheath from the prosthesis.

After retraction of the sheath has begun, the speed of retraction of the sheath is increased with reduced torque as the cords are wound around the increasing diameter of the helical cord groove. Accordingly, the sheath is easily and quickly retracted thus rapidly completing deployment of the prosthesis. Further, since dynamical frictional forces are less than static frictional forces, less torque is needed to continue retraction of the sheath and deploy the prosthesis. This allows the size and power of the motor that winds in the cords to be minimized thus minimizing the size and cost of the delivery system.

Embodiments are best understood by reference to the following detailed description when read in conjunction with the accompanying drawings.

BRIEF DESCRIPTION OF DRAWINGS

FIG. 3 is a side perspective view of a variable speed retraction mechanism in a pre-deployment position corresponding with the view of FIG. 1 in accordance with one embodiment.

FIG. 4 is a top perspective view of the variable speed retraction mechanism in the pre-deployment position corresponding with the view of FIG. 3 in accordance with one embodiment.

Common reference numerals are used throughout the drawings and detailed description to indicate like elements.

DETAILED DESCRIPTION

Figure 1:
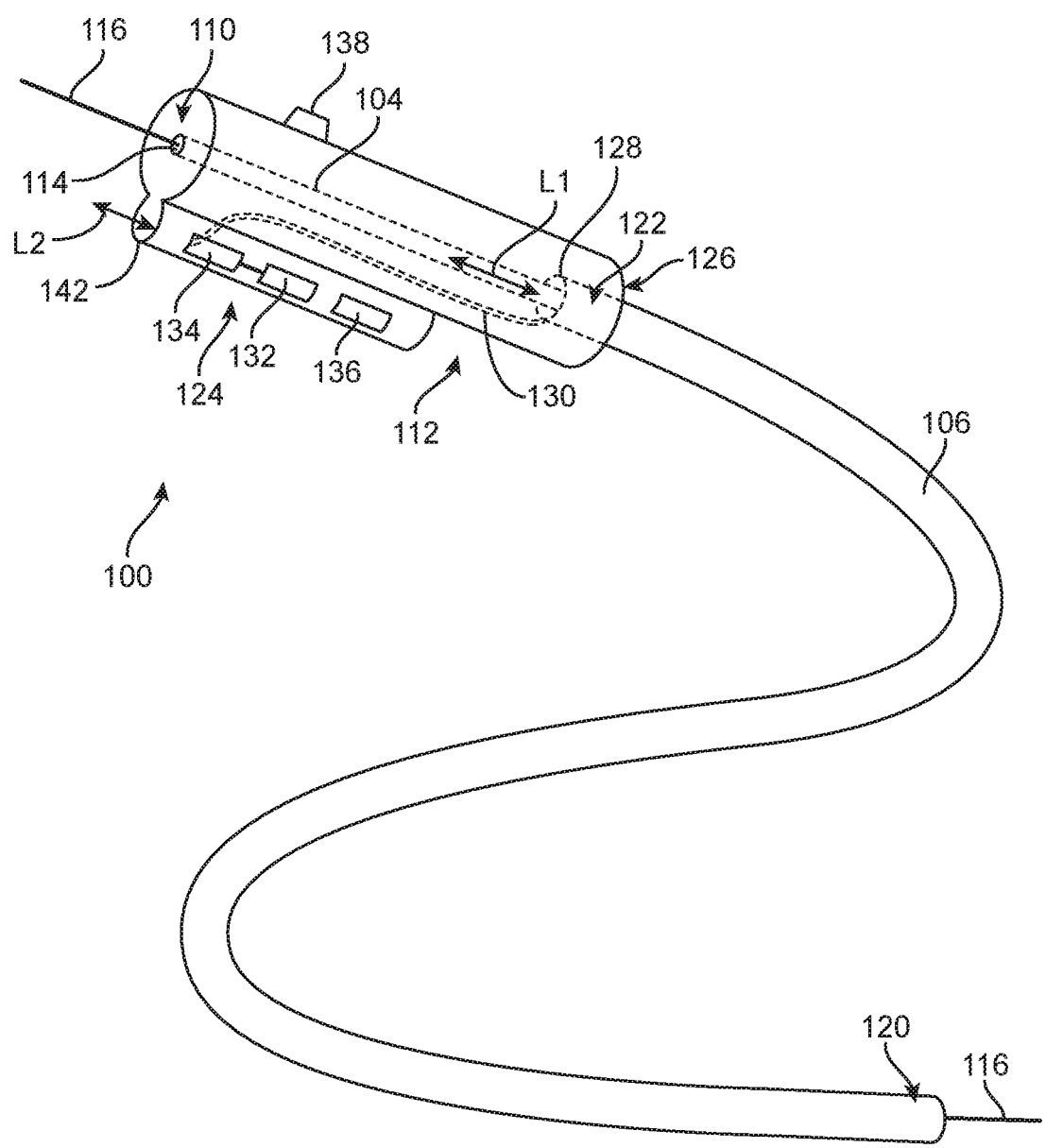
FIG. 1 is a perspective view of a delivery system for deploying a prosthesis in a pre-deployment position in accordance with one embodiment.
Figure 2:
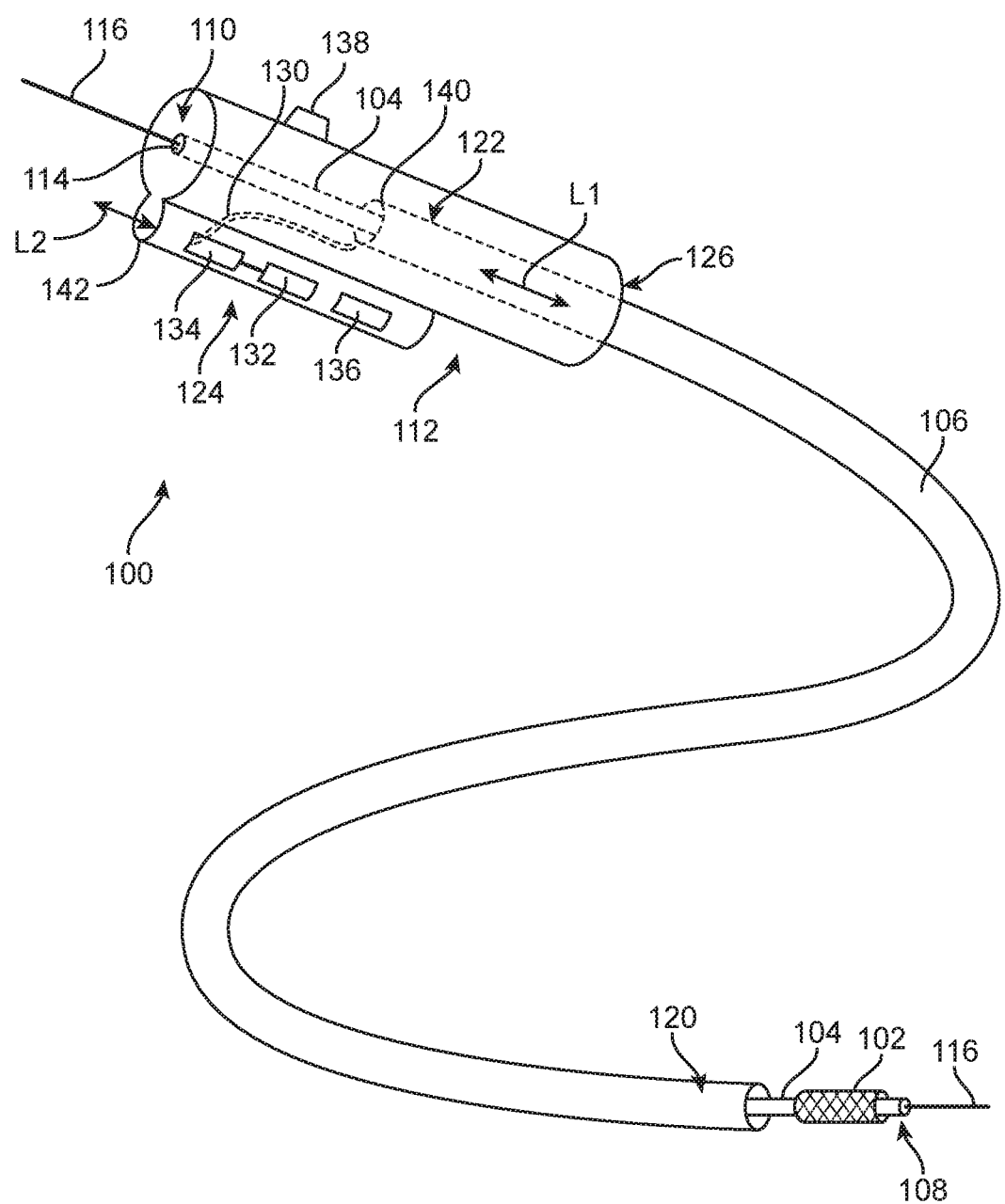
FIG. 2 is a perspective view of the delivery system during deployment of the prosthesis and in a deployment position in accordance with one embodiment.
Figure 6:
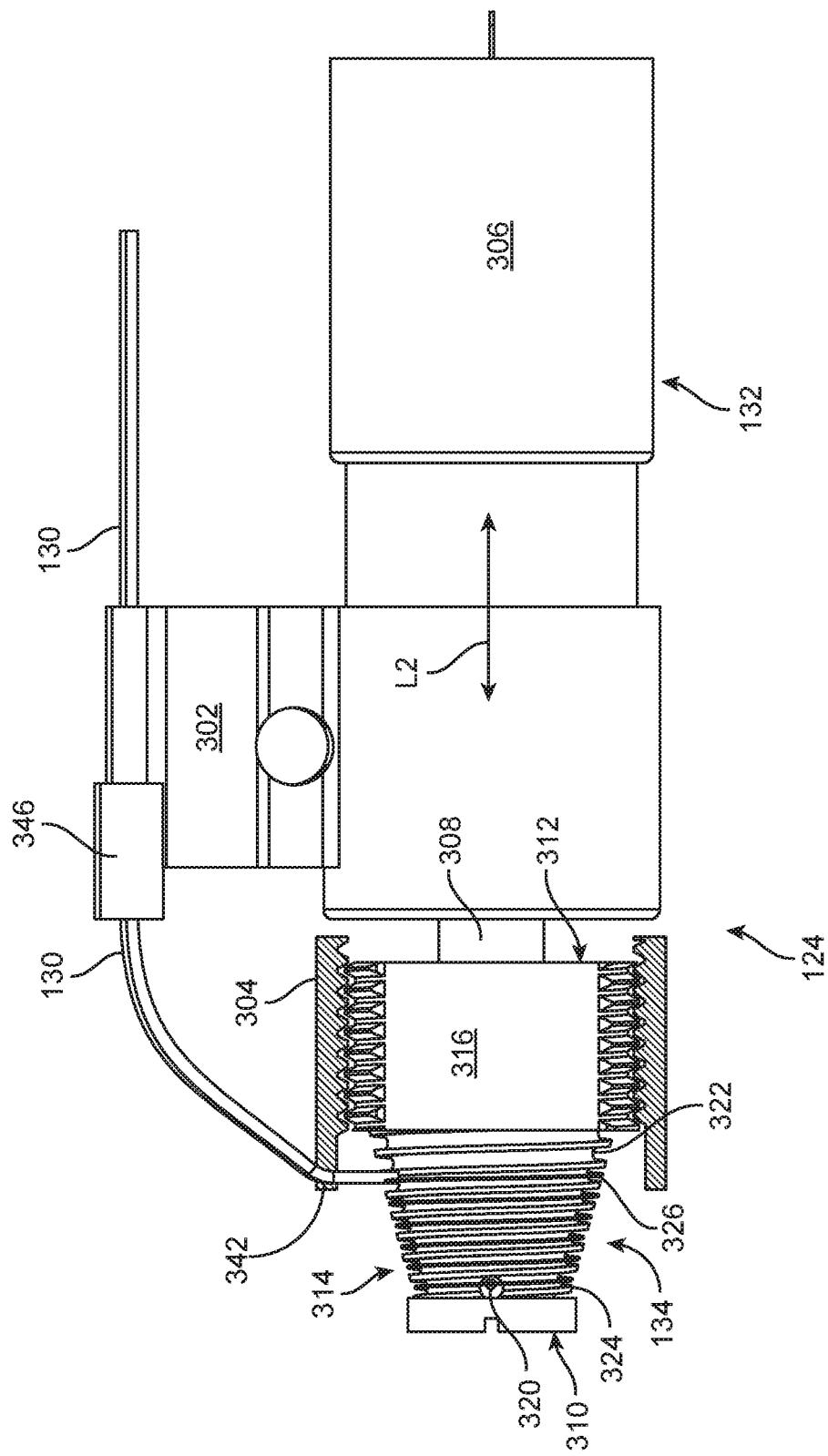
FIG. 6 is a side perspective view of the variable speed retraction mechanism in a deployment position corresponding with the view of FIG. 2 in accordance with one embodiment.

As an overview and in accordance with one embodiment, FIGS. 1 and 3 illustrate a pre-deployment position of a sheath 106 prior to retraction and FIGS. 2 and 6 illustrate retraction of sheath 106 to a deployment position for deployment of a prosthesis 102. Sheath 106 is retracted by winding in one or more cords 130 coupled to sheath 106.

More particularly, a helical reel 134 is rotated to wind cords 130 into a helical cord groove 322 and retract sheath 106. Rotation of helical reel 134 simultaneously causes a cord feed ring 304 to slide ensuring that cords 130 are correctly fed into helical cord groove 322 through cord feedthrough apertures 342 of cord feed ring 304.

Further, as shown in FIG. 3, due to the small diameter D1 of helical cord groove 322, cords 130 are retracted slowly and with a high amount of torque, e.g., a high mechanical advantage. After retraction of sheath 106 has begun, the speed of retraction of sheath 106 is increased with reduced torque as cords 130 are wound around the increasing diameter of helical cord groove 322. In other words, the retraction speed of sheath 106 increases during retraction.

Now in more detail, FIG. 1 is a perspective view of a delivery system 100 for deploying a prosthesis 102 (see FIG. 2) in a pre-deployment position in accordance with one embodiment. FIG. 2 is a perspective view of delivery system 100 during deployment of prosthesis 102 and in a deployment position in accordance with one embodiment. For example, prosthesis 102 is a radially expandable tubular prosthesis such as a stent, a stent-graft or other endovascular prosthesis and is used to treat one of several vascular conditions: abdominal aortic aneurysms, thoracic aortic aneurysm, thoracic aortic dissections, or other vascular conditions.

Referring now to FIGS. 1 and 2 together, delivery system 100 includes a pushrod 104 and a sheath 106, sometimes called a catheter sheath. Pushrod 104 includes a distal end 108 and a proximal end 110. Prosthesis 102 is placed over a portion of the distal end 108 of pushrod 104. In one embodiment, distal end 108 further includes radiopaque markers that allow the location of distal end 108 and prosthesis 102 to be determined. Proximal end 110 of pushrod 104 terminates within and is mounted to a handle 112 or extends through handle 112 and out a port 114 of handle 112.

For purposes of clarity of discussion, as used herein, the distal end of delivery system 100 is the end that is farthest from the operator (the end furthest from handle 112) while the distal end of prosthesis 102 is the end nearest the operator (the end nearest handle 112), i.e., the distal end of delivery system 100 and the proximal end of prosthesis 102 are the ends furthest from handle 112 while the proximal end of delivery system 100 and the distal end of prosthesis 102 are the ends nearest handle 112. However, those of skill in the art will understand that depending upon the access location, the description of prosthesis 102 and delivery system 100 may be consistent or opposite in actual usage.

In this embodiment, pushrod 104 is a hollow tube whose interior acts as a guide wire lumen. A guide wire 116 extends through pushrod 104 and extends out distal end 108. Guide wire 116 further extends through handle 112 and out port 114.

Sheath 106 includes a distal end 120 and a proximal end 122. Prior to deployment, prosthesis 102 is radially compressed and restrained within distal end 120 of sheath 106. Proximal end 122 of sheath 106 extends into handle 112. As discussed further below, proximal end 122 of sheath 106 is coupled to a variable speed retraction mechanism 124 of handle 112. Sheath 106 is a hollow tube which acts as a pushrod lumen. Pushrod 104 extends through sheath 106. Pushrod 104 and sheath 106 have a longitudinal axis L1 within handle 112.

During use, prosthesis 102 is placed over a portion of distal end 108 of pushrod 104 and is radially compressed and restrained within distal end 120 of sheath 106 as illustrated in FIG. 1. Prosthesis 102 is introduced intra-vascularly and guided to the treatment site, e.g., an aneurysm. Once prosthesis 102 is properly positioned, sheath 106 is retracted by handle 112 thus deploying prosthesis 102 as illustrated in FIG. 2.

More particularly, referring to FIG. 1, prior to retraction of sheath 106, proximal end 122 of sheath 106 is located towards or adjacent a distal end 126 of handle 112 as indicated by a pre-deployment position 128 of proximal end 122. When proximal end 122 of sheath 106 is at pre-deployment position 128, prosthesis 102 is radially compressed and restrained within distal end 120 of sheath 106.

Proximal end 122 of sheath 106 is coupled to variable speed retraction mechanism 124 by one or more cords 130, e.g., two cords 130. Variable speed retraction mechanism 124 includes an electric motor 132, a helical reel 134, and a battery 136 to power motor 132. Motor 132 is activated by an external switch 138, e.g., by the user, e.g., physician, of delivery system 100.

Activation of motor 132 by switch 138 causes helical reel 134 to be rotated thus winding in cords 130. As cords 130 are attached to proximal end 122 of sheath 106, retraction of cords 130 causes retraction of proximal end 122 of sheath 106 from pre-deployment position 128 (FIG. 1) to a deployment position 140 as shown in FIG. 2. Deployment position 140 of proximal end 122 of sheath 106 is farther (more proximal) from distal end 126 of handle 112 than pre-deployment position 128.

In the embodiment of FIGS. 1 and 2, an outer housing 142 of handle 112 is transparent allowing visualization of the various components therein. However, in another embodiment, housing 142 is opaque. Switch 138 is mounted to housing 142.

In one embodiment, prosthesis 102 is self-expandable. In accordance with this embodiment, as sheath 106 is retracted, the released portion of the prosthesis 102 self-expands and is permanently deployed, e.g., anchored within a lumen of a patient vessel.

As discussed below, variable speed retraction mechanism 124 initially retracts sheath 106 slowly and with high torque, also called high mechanical advantage. This allow the physician to closely monitor, fine tune, and/or adjust the deployment position for high accuracy as prosthesis 102 engages the surrounding body lumen. Further, the initial high torque overcomes the initial high static frictional forces associated with retracting sheath 106 from prosthesis 102.

After retraction of sheath 106 of has begun, variable speed retraction mechanism 124 increases the speed of retraction of sheath 106 with reduced torque. Accordingly, sheath 106 is easily and quickly retracted thus rapidly completing deployment of prosthesis 102. Further, since dynamical frictional forces are less than static frictional forces, less torque is needed to continue retraction of sheath 106 and deployment of prosthesis 102.

Figure 5:
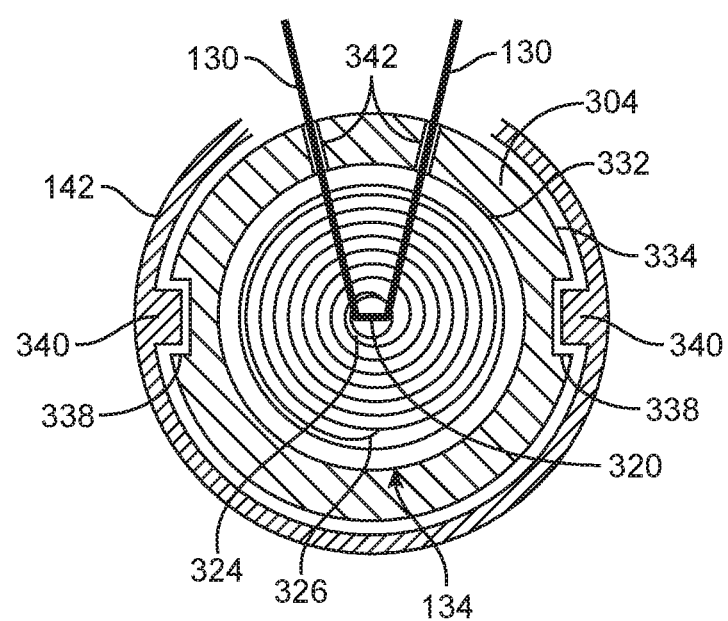
FIG. 5 is a front perspective view of the variable speed retraction mechanism along the arrow V of FIG. 3 in accordance with one embodiment.

FIG. 3 is a side perspective view of variable speed retraction mechanism 124 in a pre-deployment position corresponding with the view of FIG. 1 in accordance with one embodiment. FIG. 4 is a top perspective view of variable speed retraction mechanism 124 in the pre-deployment position corresponding with the view of FIG. 3 in accordance with one embodiment. FIG. 5 is a front perspective view of variable speed retraction mechanism 124 along the arrow V of FIG. 3 in accordance with one embodiment.

Referring now to FIGS. 1, 3-5 together, variable speed retraction mechanism 124 includes cords 130, motor 132, helical reel 134, a cord guide 302, and a cord feed ring 304. Cord feed ring 304 is illustrated in cross-section in FIG. 3 and has been removed from the view of FIG. 4 to allow visualization of the features therein. Helical reel 134 is proximal of motor 132.

In one embodiment, motor 132 is an electromagnetic motor that is powered by battery 136 as activated by switch 138. Motor 132 includes an outer housing 306 and an axle 308. Outer housing 306 of motor 132 is mounted, e.g., using screws, adhesive, or other mounting means, to outer housing 142 of handle 112. Accordingly, outer housing 306 is held stationary with respect to outer housing 142 of handle 112.

During operation of motor 132, axle 308 is rotated. Helical reel 134 is coupled to and supported on axle 308. Accordingly, rotation of axle 308 causes helical reel 134 to rotate.

Helical reel 134 includes a proximal end 310 and a distal end 312. Distal end 312 is coupled to axle 308 of motor 132, e.g., axle 308 extends into helical reel 134 from distal end 312.

Helical reel 134 includes a variable diameter cord take up section 314 and a uniform diameter cord feed ring section 316. Cord take up section 314 has a variable diameter with a minimum diameter D1, sometimes called a first diameter D1, at proximal end 310 and a maximum diameter D2, sometimes called a second diameter D2, at an interface 318 between cord take up section 314 and cord feed ring section 316. Cord take up section 314 increases in diameter uniformly from diameter D1 to diameter D2, although in another embodiment, increases in diameter non-uniformly. Cord feed ring section 316 has a uniform diameter equal to maximum diameter D2 in accordance with this embodiment. Diameter D2 is greater than diameter D1.

Although various features may be described as being parallel, perpendicular, equal in size, or having other relationships, in light of this disclosure, those of skill in the art will understand that the various features may not be exactly parallel, perpendicular, or equal, e.g., due to manufacturing tolerances. Further, the various features may have protrusions and/or indentations.

At proximal end 310, helical reel 134 includes one or more cord engagement aperture(s) 320. Cord engagement aperture 320 extends entirely through helical reel 134 in a perpendicular direction to a longitudinal axis L2 of helical reel 134 and axle 308. Cord engagement aperture 320 has a diameter large enough to accommodate passage of cords 130 therethrough.

In one embodiment, cords 130 are parts of a single integral cord, e.g., a string, that is passed through cord engagement aperture 320. By using a single integral string, the string can slide within cord engagement aperture 320 thus removing any slack between cords 130, i.e., to prevent one of cords 130 from being loose while the other cord 130 is tight. However, in other embodiments, one or more cords 130 are attached to helical reel 134 and proximal end 122 of sheath 106 using any one of a number of mounting structures, e.g., adhesive, screws, clamps, knots, welds, or other mounting structures.

Cord take up section 314 includes a helical cord groove 322 on the outer surface. Helical cord groove 322 is spiral increasing in diameter from diameter D1 at proximal end 310 to diameter D2 at interface 318. In one embodiment, helical cord groove 322 is a three-dimensional curve that lies on the surface of a cone so that its angle relative to a plane perpendicular to longitudinal axis L2 is constant. Helical cord groove 322 is a groove, sometimes called a thread, channel, indentation, or guide, that is sized to accommodate cords 130 therein. In one embodiment, helical cord groove 322 includes a thread pitch P1. Thread pitch P1 is the distance between threads of helical cord groove 322.

Generally, helical cord groove 322 has a start 324 at proximal end 310 and cord engagement aperture 320 and an end 326 at interface 318. In another embodiment, instead of single helical cord groove 322, cord take up section 314 includes one or more adjacent helical cord grooves 322.

Cord feed ring section 316 has a uniform diameter thread 328 on the outer surface. In accordance with this embodiment, thread 328 is formed as two discrete threaded sections 328A, 328B opposite one another with non-threaded sections 330 in between. However, in another embodiment, thread 328 is formed as a single continuous thread around the entire outer surface of cord feed ring section 316.

In one embodiment, thread 328 is a three-dimensional curve (either separated as illustrated in the figures or continuous) that lies on the surface of a cylinder so that its angle relative to a plane perpendicular to longitudinal axis L2 is constant. Thread 328 includes a thread pitch P1 equal to thread pitch P1 helical cord groove 322 in accordance with this embodiment.

Cord feed ring 304 is a substantially uniform diameter tube having a cylindrical inner surface 332 and a cylindrical outer surface 334. Inner surface 332 of cord feed ring 304 is threaded and includes a thread 336. Thread 336 of cord feed ring 304 is threadedly engaged with thread 328 of helical reel 134.

Paying particular attention to FIG. 5, outer surface 334 of cord feed ring 304 includes one or more housing engagement slots 338 engaged with outer housing 142 of handle 112. In accordance with this embodiment, housing engagement slots 338 including opposing slots extending along the length of outer surface 334 in a direction parallel to longitudinal axis L2. Outer housing 142 of handle 112 includes complimentary protruding ribs 340 which fit into and are engaged with housing engagement slots 338.

Housing engagement slots 338 and protruding ribs 340 enable cord feed ring 304 to move in the distal direction parallel to longitudinal axis L2. At the same time, housing engagement slots 338 and protruding ribs 340 prevent cord feed ring 304 from rotating. Although housing engagement slots 338 and protruding ribs 340 are illustrated and discussed as a slidable coupling between cord feed ring 304 and outer housing 142, in other embodiments, other slidable couplings are used. Generally, cord feed ring 302 is longitudinally slidably engaged with outer housing 142.

Cord feed ring 304 includes one or more cord feedthrough apertures 342, e.g., equal to the number of cords 130. In accordance with one embodiment, cord feedthrough apertures 342 extend from outer surface 334 to inner surface 332 of cord feed ring 304, e.g., in a radial direction. In accordance with this embodiment, there are two cord feedthrough apertures 342 corresponding to each of two cords 130.

Cord feedthrough apertures 342 can be discrete openings through which cords 130 are fed. In another embodiment, cord feedthrough apertures 342 include slots or grooves at a proximal end 344 of cord feed ring 304 allowing cords 130 to be easily slipped within cord feedthrough apertures 342.

As illustrated in FIG. 3, in the pre-deployment position, cord feedthrough apertures 342 are aligned, e.g., are the same position along the longitudinal axis L2, with start 324 of helical cord groove 322. During operation, cords 130 are guided into helical cord groove 322 through cord feedthrough apertures 342.

More particularly, the physician activates motor 132 using switch 138. Motor 132 rotates helical reel 134. Rotation of helical reel 134 causes cord feed ring 304 along with cord feedthrough apertures 342 to move distally. At the same time, rotation of helical reel 134 causes cords 130 to wrap around helical cord groove 322. As the pitch P1 of threads 328 is equal to the pitch P1 of helical cord groove 322, cord feedthrough apertures 342 remain aligned with the position where cords 130 are feeding, e.g., wound, into helical cord groove 322. In other words, cord feedthrough apertures 342 ensure that cords 130 are correctly fed into helical cord groove 322 thus avoiding cords 130 from jumping track and the associated malfunction of delivery system 100.

FIG. 6 is a side perspective view of variable speed retraction mechanism 124 in a deployment position corresponding with the view of FIG. 2 in accordance with one embodiment. Referring now to FIG. 6, variable speed retraction mechanism 124 is illustrated in the deployment position. As shown in FIG. 6, cords 130 have been wrapped around helical cord groove 322. At the same time, cord feed ring 304 has moved distally ensuring that that cords 130 are correctly fed into helical cord groove 322.

Cords 130 extend from cord feed ring 304 and cord feedthrough apertures 342 to cord guide 302. In one embodiment, cord guide 302 is mounted to outer housing 306 of motor 132. Cord guide 302 includes one or more hollow cord guides 346. In one embodiment, cord guides 346 are hollow cylinders having an axis parallel to the longitudinal axis L2. Cords 130 extend through cord guides 346. Cords 130 extend from cord guides 346 to proximal end 122 of sheath 106 as illustrated in FIGS. 1 and 2.

In one embodiment, longitudinal axis L1 of pushrod 104 and sheath 106 is parallel to longitudinal axis L2 of helical reel 134. Cords 130 extend from and are wound into helical reel 134 in a direction perpendicular to longitudinal axis L2 and thus in a direction perpendicular to longitudinal axis L1. Cords 130 extend through cord feed ring 304 and cord guide 302 to be parallel to longitudinal axis L1 at sheath 106. Cord feed ring 304 and cord guide 302 change the direction of cords from being perpendicular to longitudinal axis L1 to a direction parallel to the longitudinal axis L1.

By having helical reel 134 and motor 132 lie upon longitudinal axis L2, helical reel 134 and motor 132 extend in the length direction of handle 112. This allows handle 112 to be formed with a minimal size and to fit comfortably within the hand of the physician.

In one embodiment, motor 132 rotates helical reel 134 at a uniform rotational velocity. As shown in FIG. 3, initially, due to the small diameter D1 of helical cord groove 322, cords 130 are retracted slowly and with a high amount of torque, e.g., a high mechanical advantage. This allow the physician to closely monitor, fine tune, and/or adjust the deployment position for high accuracy as prosthesis 102 engages the surrounding body lumen. Further, the initial high torque overcomes the initial high static frictional forces associated with retracting sheath 106 from prosthesis 102. The forces required to expose prosthesis 102 are considerably higher initially than the forces are when prosthesis 102 is nearly release.

After retraction of sheath 106 has begun, variable speed retraction mechanism 124 increases the speed of retraction of sheath 106 (which is desirable) with reduced torque as cords 130 are wound around the increasing diameter of helical cord groove 322. In other words, the retraction speed of sheath 106 increases during retraction while motor 132 continues to rotate helical reel 134 at a uniform rotational velocity. Accordingly, sheath 106 is easily and quickly retracted thus rapidly completing deployment of prosthesis 102.

Further, since dynamical frictional forces are less than static frictional forces, less torque is needed to continue retraction of sheath 106 and deployment of prosthesis 102. This allows the size and power of motor 132 to be minimized thus minimizing the size and cost of delivery system 100.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A delivery system comprising:
    a sheath;
    a helical reel comprising:
        a proximal end;
        a distal end;
        a cord take up section; and
        a cord feed ring section comprising a thread on an outer surface of the cord feed ring section, wherein the cord take up section extends from the proximal end to an interface between the cord take up section and the cord feed ring section, the cord feed ring section extending from the interface to the distal end;
    a cord feed ring comprising a thread on an inner surface of the cord feed ring, the thread of the cord feed ring being threadedly engaged with the thread of the cord feed ring section;
    a cord extending from the cord take up section through a cord feedthrough aperture of the cord feed ring and to the sheath; and
    a prosthesis restrained within a distal end of the sheath.

2. The delivery system of claim 1 further comprising:
    a pushrod extending through the sheath, wherein the prosthesis is over a distal end of the pushrod.

3. The delivery system of claim 1 further comprising a variable speed retraction mechanism comprising:
    the helical reel;
    the cord;
    an electric motor, the helical reel being mounted on an axle of the motor; and
    the cord feed ring.

4. The delivery system of claim 3 further comprising:
    a handle comprising a housing, wherein the motor is mounted to the housing.

5. The delivery system of claim 4 further comprising:
    a battery configured to power the motor; and
    a switch mounted to the housing, the switch configured to activate the motor.

6. The delivery system of claim 1 wherein the cord take up section has a variable diameter increasing uniformly from a first diameter to a second diameter, the cord take up section comprising a helical cord groove on an outer surface.

7. The delivery system of claim 6 wherein the cord is attached to a start of the helical cord groove.

8. The delivery system of claim 6 wherein the helical cord groove has a thread pitch.

9. The delivery system of claim 1 wherein the cord feed ring comprises housing engagement slots, the delivery system further comprising:
    a handle comprising a housing, the housing comprising protruding ribs engaged with the housing engagement slots.

10. The delivery system of claim 1 further comprising a cord guide, the cord extending from the cord feedthrough aperture to the cord guide.

11. A delivery system comprising:
    a sheath;
    a helical reel comprising:
        a cord take up section comprising a helical cord groove on an outer surface of the helical reel, wherein the helical cord groove has a thread pitch; and
        a cord feed ring section comprising a uniform diameter thread on the outer surface comprising a thread pitch equal to the thread pitch of the helical cord groove;
    a cord feed ring threadedly engaged with the cord feed ring section;
    a cord extending from the cord take up section through a cord feedthrough aperture of the cord feed ring and to the sheath; and
    a prosthesis restrained within a distal end of the sheath.

* * * * *